United States Patent [19]
Yeh et al.

[11] Patent Number: 5,701,174
[45] Date of Patent: Dec. 23, 1997

[54] TEMPLATE MASK FOR ASSISTING IN OPTICAL INSPECTION OF OXIDATION INDUCED STACKING FAULT (OISF)

[75] Inventors: Ching Hua Yeh; Shun-Long Chen, both of Hsin-Chu, Taiwan

[73] Assignee: Taiwan Semiconductor Manufacturing Company Ltd., Hsin-Chu, Taiwan

[21] Appl. No.: 679,914

[22] Filed: Jul. 15, 1996

[51] Int. Cl.⁶ .................... G01N 21/00; G01N 21/55
[52] U.S. Cl. .................... 356/237; 356/445; 356/337
[58] Field of Search ...................... 356/237, 445, 356/337, 345, 386, 338, 342, 340, 429–431, 371, 376; 250/310, 307, 397, 309, 429.21, 441.11, 491.1

[56] References Cited

U.S. PATENT DOCUMENTS

| | | | |
|---|---|---|---|
| 3,658,420 | 4/1972 | Axelrod | 356/71 |
| 4,000,949 | 1/1977 | Watkins | 356/165 |
| 4,618,938 | 10/1986 | Sandland et al. | 364/552 |
| 5,162,867 | 11/1992 | Kohno | 356/237 |
| 5,194,743 | 3/1993 | Aoyama et al. | 250/548 |
| 5,233,203 | 8/1993 | Haga | 250/571 |
| 5,264,912 | 11/1993 | Vaught et al. | 356/237 |
| 5,377,002 | 12/1994 | Malin et al. | 356/237 |
| 5,428,442 | 6/1995 | Lin et al. | 356/237 |
| 5,444,529 | 8/1995 | Tateiwa | 356/337 |
| 5,448,350 | 9/1995 | Kohno | 356/237 |
| 5,502,306 | 3/1996 | Meisburger et al. | 250/310 |
| 5,585,918 | 12/1996 | Takeuchi et al. | 356/237 |

OTHER PUBLICATIONS

VLSI Technology, S.M. Sze, McGraw–Hill, 1988, pp. 133–135 no month available.

*Primary Examiner*—Frank G. Font
*Assistant Examiner*—Michael P. Stafira
*Attorney, Agent, or Firm*—George O. Saile; Stephen B. Ackerman; Alek P. Szecsy

[57] ABSTRACT

A method for optically inspecting a semiconductor substrate for defects such as oxidation induced stacking faults, and a template mask which assists in practicing the optical inspection method. There is first provided a semiconductor substrate which has a surface to be inspected for defects such as oxidation induced stacking faults. Aligned then upon the surface of the semiconductor substrate to be inspected for defects such as oxidation induced stacking faults is a template mask. The template mask has a minimum of one aperture which leaves exposed a portion of the surface of the semiconductor substrate to be inspected for defects such as oxidation induced stacking faults. Finally, there is inspected optically the portion of the surface of the semiconductor substrate exposed through the aperture.

10 Claims, 1 Drawing Sheet

TEMPLATE MASK FOR ASSISTING IN OPTICAL INSPECTION OF OXIDATION INDUCED STACKING FAULT (OISF)

BACKGROUND OF THE INVENTION

1. Field of the Invention

The present invention relates generally to optical inspection of semiconductor substrates. More particularly, the present invention relates to a template mask which assists in optical inspection within semiconductor substrates of defects such as, but not limited to, oxidation induced stacking faults.

2. Description of the Related Art

In conjunction with the process by which resistors, transistors, diodes and other electrical circuit elements are formed within and/or upon a semiconductor substrate, it is common in the art of integrated circuit fabrication to form directly upon the surface of the semiconductor substrate an oxide layer. Oxide layers formed directly upon semiconductor substrates typically serve either to isolate active regions of the semiconductor substrate or to provide capacitive gate oxide dielectric layers within field effect transistors (FETs). Commonly, although not exclusively, oxide layers formed directly upon semiconductor substrates within integrated circuits are formed through a thermal oxidation method where a portion of the semiconductor substrate is consumed to form within and/or upon the semiconductor substrate an oxide layer.

Although the thermal oxidation method for forming oxide layers upon semiconductor substrates is quite common in the art, the thermal oxidation method for forming oxide layers upon semiconductor substrates is not entirely without problems. In particular, it is known in the art that the thermal oxidation method for forming oxide layers upon semiconductor substrates suffers from the simultaneous formation of oxidation induced stacking faults within portions of the semiconductor substrate above which is desired to form the oxide layer. The mechanism by which oxidation induced stacking faults are formed within semiconductor substrates incident to forming through thermal oxidation methods oxide layers upon those semiconductor substrates is also known in the art. See, for example S. M. Sze, VLSI Technology, McGraw-Hill 1988, pp. 133-35, wherein it is disclosed that oxidation induced stacking faults are formed when excess silicon atoms present at the silicon-silicon oxide interface incident to forming through a thermal oxidation method an oxide layer upon a semiconductor substrate nucleate at crystalline defects within the semiconductor substrate, thus forming oxidation induced stacking faults.

The presence of oxidation induced stacking faults within silicon semiconductor substrates is sufficiently common such that generalized test methods have been developed for inspecting silicon semiconductor substrates for those oxidation induced stacking faults. A particularly common, although not exclusive, test method is disclosed by the American Society for the Testing of Materials (ASTM) as test method F416-84, the teachings of which are incorporated herein fully by reference. The generalized test methods, including the ASTM F416-84 method, provide for optical microscopic inspection of several test sites upon a silicon semiconductor substrate upon whose surface is formed an oxide layer through a thermal oxidation method. Although the general methods provide a convenient and standardized means for determining oxidation induced stacking fault areal density within silicon semiconductor substrates, generalized optical microscopic inspection methods, such as the ASTM F416-84 method, are not entirely without problems. For example, the general optical microscopic inspection methods suffer from deficiencies including but not limited to: (1) an inability to exactly define the positions and boundaries of the various sample locations upon a silicon semiconductor substrate to be inspected; (2) an inability to adequately focus an optical microscope through the various sample locations upon a semiconductor substrate to be inspected, particularly under the common circumstance where there is no patterning upon the silicon semiconductor substrate; and (3) an inconsistency in defining equivalent fields of view when employing different optical microscopes for inspecting the same semiconductor substrate. Each of these deficiencies provides genuine limitations in efficiently and reproducibly optically inspecting a silicon semiconductor substrate for defects such as oxidation induced stacking faults through standardized test methods, such as the ASTM F416-84 method.

Thus, it is desirable in the art to provide a simple and uniform optical method and apparatus for inspecting silicon semiconductor substrates for defects such as oxidation induced stacking faults, where the method and apparatus avoids the several deficiencies as noted above. It is towards that goal that the present invention is directed.

Methods and apparatus through which various inspections of semiconductor substrates may be efficiently undertaken are disclosed in the art. For example, Sandland et al. in U.S. Pat. No. 4,618,938 disclose an automated semiconductor substrate inspection apparatus which includes a system computer to provide functions including both: (1) data storage; and (2) movement of the semiconductor substrate. In addition, Haga in U.S. Pat. No. 5,233,203 discloses an additional automated semiconductor substrate inspection apparatus through which the field of view of an optical microscope is moved uniformly along the surface of the semiconductor substrate. Finally, Tateiwa in U.S. Pat. No. 5,444,529 discloses a method for inspecting particles on semiconductor substrates where the particles act as condensation nuclei to form water droplets which more efficiently scatter laser light employed in inspection of the semiconductor substrate.

Desirable in the art are additional methods and apparatuses through which semiconductor substrates may be inspected for defects such as, but not limited to, oxidation induced stacking faults. Particularly desirable are optical microscopic inspection methods through which the areal density of oxidation induced stacking faults within semiconductor substrates may be determined while simultaneously: (1) easily defining the positions and boundaries of the various sample locations upon a semiconductor substrate to be inspected; (2) easily focusing an optical microscope upon the various sample locations upon a semiconductor substrate to be inspected, even under conditions where there is no patterning upon the semiconductor substrate; and (3) providing consistency in defining equivalent fields of view even when different optical microscopes are employed when inspecting the same semiconductor substrate.

SUMMARY OF THE INVENTION

A first object of the present invention is to provide a method for optically microscopically inspecting a semiconductor substrate for defects such as oxidation induced stacking faults while easily defining the positions and boundaries of the various sample locations upon the semiconductor substrate to be inspected.

A second object of the present invention is to provide a method for optically microscopically inspecting a semiconductor substrate for defects such as oxidation induced stacking faults while easily focusing an optical microscope upon the various sample locations upon a semiconductor substrate to be inspected, even under conditions where there is no patterning upon the semiconductor substrate.

A third object of the present invention is to provide a method for optically microscopically inspecting a semiconductor substrate for defects such as oxidation induced stacking faults while providing consistency in defining equivalent fields of view even when different optical microscopes are employed when inspecting the same semiconductor substrate.

In accord with the objects of the present invention, there is provided by the present invention a method for optically microscopically inspecting a semiconductor substrate for defects such as oxidation induced stacking faults, as well as a template mask which is employed in assisting the optical microscopic inspection of the semiconductor substrate. To practice the method of the present invention, there is provided a semiconductor substrate which has a surface desired to be inspected for defects such as oxidation induced stacking faults. There is then aligned upon the surface of the semiconductor substrate to be inspected for defects such as oxidation induced stacking faults a template mask. The template mask has at least one aperture formed therein which leaves exposed a portion of the surface of the semiconductor substrate to be inspected for defects such as oxidation induced stacking faults. Finally, the portion of the surface of the semiconductor substrate exposed through the aperture is optically inspected.

The present invention provides a method for optically microscopically inspecting semiconductor substrates for defects such as oxidation induced stacking faults while: (1) easily defining the positions and boundaries of the various sample locations upon a semiconductor substrate to be inspected; (2) easily focusing an optical microscope upon the various sample locations upon a semiconductor substrate to be inspected, even under conditions where there is no patterning upon the semiconductor substrate; and (3) providing consistency in defining equivalent fields of view even when different optical microscopes are employed when inspecting the same semiconductor substrate.

Through the template mask employed within the method of the present invention, there is exposed at least one area of a semiconductor substrate aligned beneath the template mask, which area is to be inspected for defects such as, but not limited to, oxidation induced stacking faults. The template mask when employed within the method of the present invention reproducibly defines the positions and boundaries of the sample location(s) upon a semiconductor substrate to be inspected. In addition, the template mask when employed within the method of the present invention also provides a edge upon which an optical microscope field of view may be focused. Thus, there is provided through the method of the present invention a means for easily focusing an optical microscope upon the sample location(s) upon a semiconductor substrate to be inspected, even under conditions where there is no patterning upon the semiconductor substrate. Finally, the template mask when employed within the method of the present invention defines the limits of the field of view for sample location(s) upon a semiconductor substrate to be inspected. Thus, consistency is provided through the method of the present invention in defining equivalent fields of view even when different optical microscopes are employed when inspecting the same semiconductor substrate.

BRIEF DESCRIPTION OF THE DRAWINGS

The objects features and advantages of the present invention are understood within the context of the Description of the Preferred Embodiments, as set forth below. The Description of the Preferred Embodiments is understood within the context of the accompanying drawings, which form a material part of this disclosure, wherein.

DESCRIPTION OF THE PREFERRED EMBODIMENTS

The present invention provides a method for optically microscopically inspecting semiconductor substrates for defects such as oxidation induced stacking faults while: (1) easily defining the positions and boundaries of the various sample locations upon a semiconductor substrate to be inspected; (2) easily focusing an optical microscope upon the various sample locations upon the semiconductor substrate to be inspected, even under conditions where there is no patterning upon the semiconductor substrate; and (3) providing consistency in defining equivalent fields of view even when different optical microscopes are employed when inspecting the same semiconductor substrate. The method of the present invention achieves these objects by employing a template mask which defines the positions and boundaries of a semiconductor substrate placed beneath the template mask to be optically microscopically inspected for defects such as oxidation induced stacking faults.

Although the method of the present invention and the template mask employed within the method of the present invention will typically be employed when optically microscopically inspecting semiconductor substrates for oxidation induced stacking faults (OISF), the method of the present invention and the template mask employed within the method of the present invention may alternatively be employed to inspect a semiconductor substrate or other type of substrate for defects other than oxidation induced stacking faults when the preferred inspection method requires the definition of at least one discrete inspection location upon the surface of the substrate.

The method of the present invention and the template mask of the present invention may be employed in inspecting for defects such as oxidation induced stacking faults within semiconductor substrates employed in forming various types of integrated circuits. The method of the present invention and the template mask of the present invention may be employed in inspecting for defects such as oxidation induced stacking faults within semiconductor substrates employed in forming integrated circuits including but not limited to Dynamic Random Access Memory (DRAM) integrated circuits, Static Random Access Memory (SRAM) integrated circuits, Application Specific Integrated Circuits (ASICs), integrated circuits having within their fabrications field effect transistors (FETs), integrated circuits having within their fabrications bipolar transistors and integrated circuits having within their fabrications Bipolar Complementary Metal Oxide Semiconductor (BiCMOS) transistors.

Figure 1:
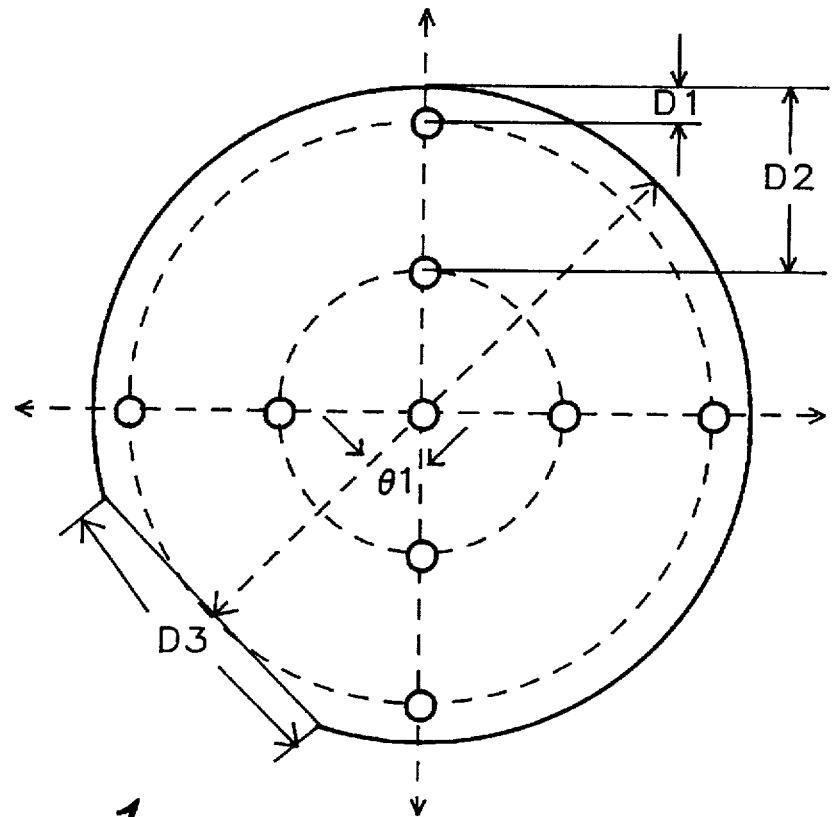
FIG. 1 shows a schematic plan-view diagram of a first template mask to be employed in inspecting the surface of a six inch diameter semiconductor substrate for defects such as oxidation induced stacking faults, the first template mask being employed within a first preferred embodiment of the method of the present invention.
Figure 2:
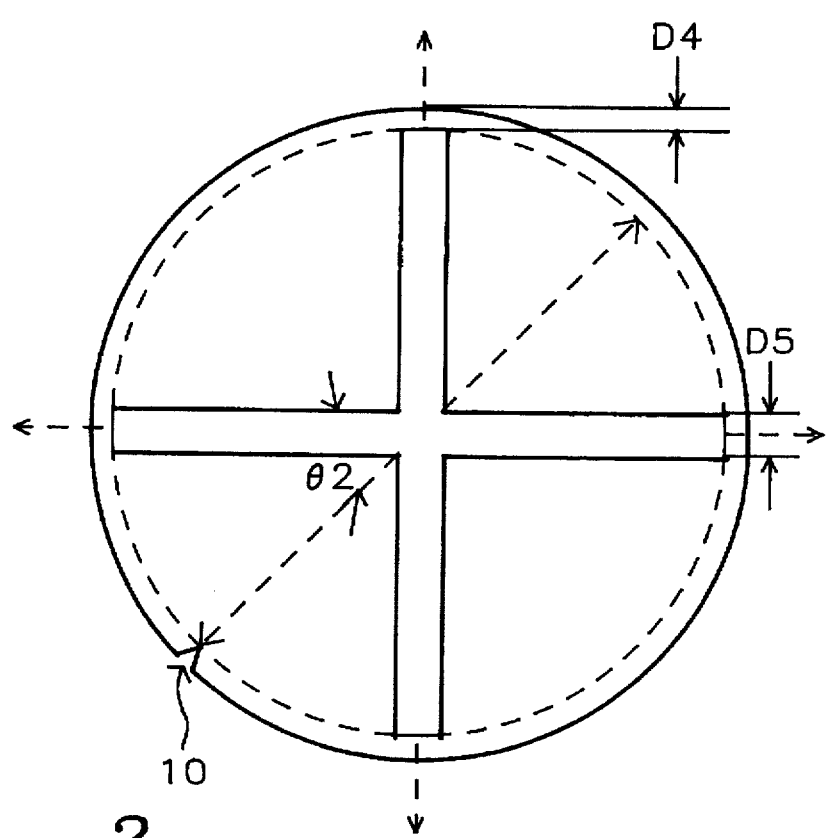
FIG. 2 shows a schematic plan-view diagram of a second template mask to be employed in inspecting the surface of an eight inch diameter semiconductor substrate for defects such as oxidation induced stacking faults, the second template mask being employed within a second preferred embodiment of the method of the present invention.

Referring now to FIG. 1 and FIG. 2, there is shown a pair of schematic plan-view diagrams illustrating a first template mask employed within a first preferred embodiment of the method of the present invention and a second template mask employed within a second preferred embodiment of the method of the present invention. The schematic plan-view diagram of the first template mask is illustrated in FIG. 1 and the schematic plan-view diagram of the second template mask is illustrated in FIG. 2. The first template mask and the second template mask differ primarily in the size of the semiconductor substrate for whose surface an inspection is assisted with the first template mask and the second template mask. The first template mask is employed in assisting an optical microscopic inspection of a six inch diameter semiconductor substrate placed beneath the first template mask. The second template mask is employed in assisting an optical microscopic inspection of an eight inch diameter semiconductor substrate placed beneath the second template mask.

Referring now to FIG. 1, there is shown a schematic plan-view diagram of the first template mask employed in assisting the inspection of defects such as oxidation induced stacking faults within a six inch diameter semiconductor substrate. As shown in FIG. 1, the first template mask has a flat edge section D3 of length about 57.5 mm, approximately equivalent to the flat edge section found on a six inch diameter semiconductor substrate. In addition, within the first template mask there is formed a series of nine circular apertures spaced to form an X, where the two portions of the X are perpendicular to each other. Further, the flat edge section D3 is centered between two adjoining terminal portions of the X, thus forming an angle θ1 of about 45 degrees with respect to the perpendicular to the flat edge section D3, as shown in FIG. 1.

As is also shown in FIG. 1, one of the nine circular apertures within the first template mask is formed at about a central location within the first template mask to leave exposed the center of a six inch diameter semiconductor substrate placed beneath the first template mask. In addition, a first series of four circular apertures is also formed within the first template mask to leave exposed four portions of the six inch diameter semiconductor substrate placed beneath the first template mask. Each of the four circular apertures within the first series of four circular apertures is formed at a location within the first template mask to leave exposed a circular aperture centered at a distance D2 about 32.5 mm from the edge of the six inch diameter semiconductor substrate placed beneath the first template mask. Finally, a second series of four apertures is also formed into the first template mask in appropriate co-linear locations to form the X pattern within the first template mask. Each of the four circular apertures within the second series of four circular apertures is formed at a location within the first template mask to leave exposed a circular aperture centered at a distance D1 about 10 mm from the edge of the six inch diameter semiconductor substrate placed beneath the first template mask. Each of the nine circular apertures within the first template mask preferably has a diameter of about 5 mm. In addition, the first template mask is designed such that the flat edge section D3 is preferably aligned with a flat edge section of the six inch diameter semiconductor substrate whose inspection is assisted with the first template mask.

Referring now to FIG. 2, there is shown a schematic plan-view diagram illustrating a second template mask employed in assisting in inspecting of defects such as oxidation induced stacking faults within an eight inch diameter semiconductor substrate. Shown in FIG. 2 is a second template mask whose edge has formed therein a notch 10. Preferably, the notch 10 has a width of about 1.1 mm to align with a notch of nominally equivalent dimension within the edge of an eight inch semiconductor substrate. The diagonal from the notch 10 to the opposite side of second template mask bisects each side of a single X shaped aperture formed into the second template mask at an angle θ2 of 45 degrees as defined in FIG. 2. Each side of the single X shaped aperture has a width D5 of about 10 mm, and each end of each side of the single X shaped aperture leaves exposed a portion of an eight inch diameter semiconductor substrate placed beneath the second template mask, where the portion of the eight inch diameter semiconductor substrate exposed beneath the second template mask terminates at a distance D4 of about 7.5 mm from the edge of the eight inch diameter semiconductor substrate. The second template mask is designed such that the notch 10 is preferably aligned with a notch in an eight inch diameter semiconductor substrate desired to be inspected with assistance of the second template mask.

Although specifically illustrated by neither FIG. 1 nor FIG. 2, the first template mask and the second template mask may be formed of several materials, including but not limited to metals, metal alloys, polymers and ceramics fabricated through methods as are conventional in the art. Preferably, the first template mask and the second template mask are formed of stainless steel. Preferably, the first template mask and the second template mask are formed from a stainless steel template mask blank of thickness about 0.3 to about 1 mm.

As is understood by a person skilled in the art, there may also be employed with the first template mask as illustrated in FIG. 1 and the second template mask as illustrated in FIG. 2 additional fixturing devices which provide for proper alignment and fixturing of the first template mask upon a six inch diameter semiconductor substrate placed beneath the first template mask or proper alignment and fixturing of the second template mask upon an eight inch diameter semiconductor substrate placed beneath the second template mask. Although specifically illustrated by neither the schematic plan-view diagram of FIG. 1 nor the schematic plan-view diagram of FIG. 2, such fixturing may take several forms as are known in the art, preferably provided that the preferred dimensional limitations with respect to the portions of the six inch diameter semiconductor substrate exposed beneath the first template mask or the portions of the eight inch diameter semiconductor substrate exposed beneath the second template mask are maintained.

Following alignment and optional fixturing of a six inch diameter semiconductor substrate placed beneath the first template mask, or alignment and optional fixturing of an eight inch diameter semiconductor substrate placed beneath the second template mask, the portions of the six inch diameter semiconductor substrate exposed through the first template mask or the portions of the eight inch diameter semiconductor substrate exposed through the second template mask may be inspected, typically and preferably by means of an optical microscope. Any of several types of optical microscopes as are conventional in the art may be employed in inspecting the portions of the six inch diameter semiconductor substrate exposed through the first template mask or the portions of the eight inch diameter semiconductor substrate exposed through the second template mask, including but not limited to monocular microscopes, binocular microscopes, light field microscopes and dark field microscopes. For the first preferred embodiment of the method of the present invention employing the first template mask and the second preferred embodiment of the method of the present invention employing the second template mask, there is preferably employed in inspecting the exposed portions of a six inch diameter semiconductor substrate or the exposed portions of an eight inch diameter semiconductor substrate a light field microscope at a magnification of about 20 to about 50 times.

As is understood by a person skilled in the art, the sizes and locations of the apertures within the first template mask and the second template mask may be modified, as required, to accommodate any of various optical inspection methods for inspecting six inch diameter semiconductor substrates and eight inch diameter semiconductor substrates for defects such as, but not limited to, oxidation induced stacking faults. Such optical inspection methods include but are not limited to the ASTM F416-84 inspection method. Typically, the variation of dimensions employed in forming the first template mask and the second template mask is defined by the inspection method which is assisted by the first template mask and the second template mask. Such dimensional variations are typically well within ±20 percent. As is also understood by a person skilled in the art, additional template masks may be designed and fabricated to accommodate semiconductor substrates of sizes other than six inch diameter semiconductor substrates and eight inch diameter semiconductor substrates, as well as other substrates which are not semiconductor substrates. These additional template masks may be formed through methods and materials analogous to the methods and materials as are employed in forming the first template mask and the second template mask, with the exception that the apertures within the additional template masks will typically and preferably be designed and fabricated to a standard not encompassed by the first template mask or the second template mask.

As is further understood by a person skilled in the art, the preferred embodiments of the method of the present invention employing the first template mask and the second template mask are illustrative of the method of the present invention employing a template mask rather than limiting of the method of the present invention by employing only the first template mask or the second template mask. Revisions may be made to the method of the present invention, including but not limited to the methods, materials, structures and dimensions through which is formed the first template mask, and the second template mask while still providing a method and a template mask in accord with the spirit and scope of the present invention, as defined by the appended claims.

What is claimed is:

1. A method for optically inspecting a semiconductor substrate for defects such as oxidation induced stacking faults comprising:

providing a semiconductor substrate, the semiconductor substrate having a surface to be inspected for defects such as oxidation induced stacking faults;

aligning the surface of the semiconductor substrate to be inspected for defects such as oxidation induced stacking faults a template mask, the template mask having a minimum of one aperture which leaves exposed a portion of the surface of the semiconductor substrate to be inspected for defects such as oxidation induced stacking faults; and inspecting optically the portion of the surface of the semiconductor substrate exposed through the aperture, while the semiconductor substrate remains fixed with respect to the template mask.

2. The method of claim 1 where the template mask is from about 0.3 to about 1 millimeters thick.

3. The method of claim 1 wherein the template mask is formed from stainless steel.

4. The method of claim 1 wherein the template mask has a diameter designed to align upon a six inch diameter semiconductor substrate placed beneath the template mask, the six inch diameter semiconductor substrate having a flat edge of about 57.5 min.

5. The method of claim 4 wherein the template mask has a series of nine circular apertures formed therein wherein:

a first one of the nine circular apertures exposes approximately the center of the six inch diameter semiconductor substrate placed beneath the template mask;

a first group of four additional circular apertures exposes a first group of four other portions of the six inch diameter semiconductor substrate whose centers are located about 32.5 mm from the edge of the six inch diameter semiconductor substrate placed beneath the template mask; and a second group of four additional circular apertures exposes a second group of four other portions of the six inch diameter semiconductor substrate whose centers are located about 10 mm from the edge of the six inch diameter semiconductor substrate placed beneath the template mask where the series of nine circular apertures forms an X where both portions of the X are perpendicular to each other and where the flat edge of the semiconductor substrate is centered between two adjoining terminal portions of the X.

6. The method of claim 5 wherein each aperture within the series of nine apertures has a diameter of about 5 mm.

7. The method of claim 1 wherein the template mask has a diameter designed to align upon an eight inch diameter semiconductor substrate placed beneath the template mask, the eight inch diameter semiconductor substrate having a notch formed within its perimeter.

8. The method of claim 7 wherein the template mask has a single aperture formed therein, the single aperture formed in an X shape where the two portions of the X shape are perpendicular to each other, each of the two portions of the X shape exposing a portion of the eight inch diameter semiconductor substrate placed beneath the template mask, the portion of the eight inch diameter semiconductor substrate ending about 7.5 mm from the edge of the semiconductor substrate, the notch being centered between an adjoining pair of end portions of the X.

9. The method of claim 8 wherein each of the portions of the X has a width of about 10 mm.

10. The method of claim 1 wherein the optical inspection is undertaken employing an optical microscope at a magnification of from about 20 to about 50 times.

* * * * *